United States Patent [19]

Bundy

[11] Patent Number: 4,477,684
[45] Date of Patent: Oct. 16, 1984

[54] 11-DEOXY-11α-ALKYL-PGE COMPOUNDS FROM PGA COMPOUNDS BY LITHIUM ALKYLATION

[75] Inventor: Gordon L. Bundy, Portage, Mich.

[73] Assignee: The Upjohn Company, Kalamazoo, Mich.

[21] Appl. No.: 391,098

[22] Filed: Jun. 23, 1982

[51] Int. Cl.³ .......................................... C07C 177/00
[52] U.S. Cl. ..................................... 568/379; 549/78; 549/498; 560/121; 562/503; 568/330; 424/305; 424/317; 424/331
[58] Field of Search ................. 568/330, 379; 549/78, 549/498

[56] References Cited

U.S. PATENT DOCUMENTS

| | | | |
|---|---|---|---|
| 4,036,871 | 7/1977 | Holland et al. | 260/468 |
| 4,052,446 | 10/1977 | Holland et al. | 260/514 |
| 4,057,571 | 11/1977 | Grudzinskas et al. | 560/121 |
| 4,059,576 | 11/1977 | Holland et al. | 542/426 |
| 4,112,225 | 9/1978 | Holland et al. | 542/426 |
| 4,187,381 | 2/1980 | Holland et al. | 560/121 |
| 4,204,074 | 5/1980 | Holland et al. | 562/503 |
| 4,227,019 | 10/1980 | Holland et al. | 562/503 |
| 4,237,276 | 12/1980 | Holland et al. | 542/426 |
| 4,246,402 | 1/1981 | Holland et al. | 542/426 |
| 4,246,426 | 1/1981 | Holland et al. | 560/231 |

OTHER PUBLICATIONS

Corey, E.J. et al., Selective Formation of Carbon—Carbon Bonds Between Unlike Groups Using Organocopper Reagents, JACS 89:3911–3912 (1967).

Crabbe, P., Application of Physical Methods to Some Structural and Stereo-Chemical Problems in the Prostaglandin Field, Tetrahedron 30:1979–1985 (1974).

Guzman, A. et al., Synthesis of Methylated Prostaglandins, Chemistry and Industry, pp. 635–636, Jul. 7, 1973.

House, H. O. et al., The Chemistry of Carbanions, XII, J. Organic Chemistry, 31:3128–3141 (1966).

*Primary Examiner*—Robert Gerstl
*Attorney, Agent, or Firm*—Robert A. Armitage

[57] ABSTRACT

The present invention provides a process for the preparation of 11α-alkylprostaglandin E compounds from corresponding prostaglandin A compounds via reaction with alkyllithium complexes, and novel 11-deoxy-11α-alkylprostaglandin E compounds useful for the same pharmacological purposes as the natural PGE compounds, e.g., antiulcer and antisecretory effects.

2 Claims, No Drawings

11-DEOXY-11α-ALKYL-PGE COMPOUNDS FROM PGA COMPOUNDS BY LITHIUM ALKYLATION

BACKGROUND OF THE INVENTION

The present invention relates to novel chemical compounds in the known series of 11-deoxy-11α-alkyl-PGE compounds.

The present invention further relates to a novel process for preparing 11-deoxy-11α-alkylprostaglandin E compounds from corresponding prostaglandin A starting materials.

11-deoxy-11α-alkyl-PGE compounds are known in the art. These compounds are prepared by methods described in numerous U.S. patents including U.S. Pat. Nos. 4,204,074; 4,227,019; 4,246,426; 4,246,402; 4,059,576; 4,036,871; 4,052,446; 4,112,225; 4,187,381; and 4,237,276. These U.S. patents, hereinafter refered to as the "Holland et al., patents" describe the preparation 11-deoxy-11α-alkylprostaglandin E compounds by total synthesis from bicyclic lactone intermediates, i.e., bicyclic lactone aldehydes or alcohols. See for example at column 16 of U.S. Pat. No. 4,246,426, wherein the preparation of 11α-alkylprostaglandin E compounds from such latent C-11 alkyl substituted bicyclic lactone aldehydes is described.

These known 11deoxy-11α-alkylprostaglandin E compounds are all known to be useful for many of the same pharmacological purposes as the natural prostaglandins. Among these purposes are antihypertensive, antiulcer, and gastric antisecretory purposes. All of the 11-deoxy-11α-methylprostaglandin E compounds prepared by the process herein are useful pharmacological agents for the purposes disclosed in the Holland et al. patents, the relevant disclosure thereof pertaining to the use of these compounds being incorporated here by reference.

PRIOR ART

11-Deoxy-11α-alkylprostaglandin E compounds are known. Refer to the Holland et al., patents described above. The use of alkyllithium, especially methyllithium complexes, to accomplish conjugate addition of alkyl groups to α,β-unsaturated ketones is known in the art. See House, H.O., et al., Journal of Organic Chemistry 31:3128 (1966) and Corey, E.J., et al., JACS 89:3911 (1967). Also, the preparation of prostaglandin E compounds from prostaglandin A compounds via alkyllithium complexes is known. See U.S. pat. No. 4,057,571 and P. Crabbe Tetr. Lett. 30:1979–1985 (1974) and Chemistry and Industry (p. 635), July 7, 1973.

SUMMARY OF THE INVENTION

The present invention particularly provides a process for preparing an 11-deoxy-11α-($C_1$-$C_4$)-alkylprostaglandin E compound of formula I
wherein $Z_1$ is
(1) cis—CH=CH—$CH_2$—$(CH_2)_g$—$C(R_2)_2$—,
(2) cis—$CH_2$CH=CH—$(CH_2)_g$—$CH_2$—,
(3) trans—$(CH_2)_2$—$(CH_2)_g$—CH=CH—,
(4) —$(CH_2)_3$—$(CH_2)_g$—$C(R_2)_2$—,
(5) —$CH_2$—O—$CH_2$—$(CH_2)_g$—$CH_2$—,
(6) —$(CH_2)_2$—O—$(CH_2)_g$—$CH_2$—,
(7) —$(CH_2)_3$—O—$(CH_2)_g$—, or
(8) —(m—Ph)—$Z_3$—$(CH_2)_g$—, wherein $R_2$ is hydrogen or fluoro, g is one, two, or three, $Z_3$ is oxa or methylene, and (m-Ph) is inter-meta-phenylene;
wherein $L_1$ is α-$R_3$:β-$R_4$, α-$R_4$:β-$R_3$, or a mixture of α-$R_3$:β-$R_4$ and a-$R_4$:β-$R_3$ wherein $R_3$ and $R_4$ are hydrogen, methyl, or fluoro, being the same or different, with the proviso that one of $R_3$ and $R_4$ is fluoro only when the other is hydrogen or fluoro and $M_1$ is α-OH:β-$R_5$ or α-$R_5$:β-OH, wherein $R_5$ is hydrogen or methyl or wherein $L_1$ is α-OH:β-$R_5$ or α-$R_5$:β-OH and $M_1$ is α-H:β-H;
wherein $R_7$ is
(1) -$C_mH_{2m}$-$CH_3$, wherein m is an integer from one to 5, inclusive,
(2) phenoxy optionally substituted by one, two or three chloro, fluoro, trifluoromethyl, ($C_1$-$C_3$)alkyl, or ($C_1$-$C_3$)alkoxy, with the proviso that not more than two substituents are other than alkyl, with the proviso that $R_7$ is phenoxy or substituted phenoxy, only when $R_3$ and $R_4$ are hydrogen or methyl, being the same or different,
(3) phenyl, benzyl, phenylethyl, or phenylpropyl optionally substituted on the aromatic ring by one, two, or three chloro, fluoro, trifluoromethyl, ($C_1$-$C_3$)alkyl, or ($C_1$-$C_3$)alkoxy, with the proviso that not more than two substituents are other than alkyl,
(4) cis—CH=CH—$CH_2$—$CH_3$,
(5) —$(CH_2)_2$—CH(OH)—$CH_3$, or
(6) —$(CH_2)_3$—CH=C$(CH_3)_2$;
wherein —C($L_1$)—$R_7$ taken together is
(1) ($C_4$-$C_7$)cycloalkyl optionally substituted by one to 3 ($C_1$-$C_5$) alkyl;
(2) 2-(2-furyl)ethyl,
(3) 2-(3-thienyl)ethoxy, or
(4) 3-thienyloxymethyl;
wherein $X_1$ is
(1) -COO$R_1$, wherein $R_1$ is
   (a) hydrogen,
   (b) ($C_1$-$C_{12}$)alkyl,
   (c) ($C_3$-$C_{12}$)cycloalkyl,
   (d) ($C_7$-$C_{12}$)aralkyl,
   (e) phenyl, optionally substituted with one, 2 or 3 chloro or ($C_1$-$C_3$)alkyl,
   (f) phenyl substituted in the para position by
      (i) —NH—CO—$R_{25}$,
      (ii) —CO—$R_{26}$,
      (iii) —O—CO—$R_{54}$, or
      (iv) —CH=N—NH—CO—$NH_2$
   wherein $R_{25}$ is methyl, phenyl, acetamidophenyl, benzamidophenyl, or —$NH_2$; $R_{26}$ is methyl, phenyl, —$NH_2$, or methoxy; and $R_{54}$ is phenyl or acetamidophenyl; inclusive, or
   (g) a pharmacologically acceptable cation;
(2) —$CH_2OH$,
(3) —CO$L_4$, wherein $L_4$ is
   (a) amino of the formula —$NR_{51}R_{52}$, wherein $R_{51}$ and $R_{52}$ are
      (i) hydrogen,
      (ii) ($C_1$-$C_{12}$)alkyl,
      (iii) ($C_3$-$C_{10}$)cycloalkyl,
      (iv) ($C_7$-$C_{12}$)aralkyl,
      (v) phenyl, optionally substituted with one, 2, or 3 chloro, ($C_1$-$C_3$)alkyl, hydroxy, carboxy, ($C_2$-$C_5$)alkoxycarbonyl, or nitro,
      (vi) ($C_2$-$C_5$)carboxyalkyl,
      (vii) ($C_2$-$C_5$)carbamoylalkyl,
      (viii) ($C_2$-$C_5$)cyanoalkyl, (ix) $(C_3-C_6)$acetylalkyl, (x) $(C_7-C_{11})$benzoalkyl, optionally substituted by one, 2 or 3 chloro, $(C_1-C_3)$alkyl, hydroxy, $(C_1-C_3)$alkoxy, carboxy, $(C_2-C_5)$alkoxycarbonyl, or nitro, (xi) pyridyl, optionally substituted by one, 2 or 3 chloro, $(C_1-C_3)$alkyl, or $(C_1-C_3)$alkoxy, (xii) $(C_6-C_9)$pyridylalkyl optionally substituted by one, 2 or 3 chloro, $(C_1-C_3)$alkyl, hydroxy, or $(C_1-C_3)$alkyl, (xiii) $(C_1-C_4)$hydroxyalkyl, (xiv) $(C_1-C_4)$dihydroxyalkyl, (xv) $(C_1-C_4)$trihydroxyalkyl, with further proviso that not more than one of $R_{51}$ and $R_{52}$ is other than hydrogen or alkyl, (b) cycloamino selected from the group consisting of pyrollidino, piperidino, morpholino, piperazino, hexamethyleneimino, pyrrollino, or 3,4-didehydropiperidinyl optionally substituted by one or 2 $(C_1-C_{12})$alkyl of one to 12 carbon atoms, inclusive, (c) carbonylamino of the formula $-NR_{53}COR_{51}$, wherein $R_{53}$ is hydrogen or $(C_1-C_4)$alkyl and $R_{51}$ is other hydrogen, but otherwise as defined above, (d) sulfonylamino of the formula $-NR_{53}SO_2R_{51}$, wherein $R_{51}$ and $R_{53}$ are as defined in (c), (4) $-CH_2NL_2L_3$, wherein $L_2$ and $L_3$ are hydrogen or $(C_1-C_4)$alkyl, being the same or different, or the pharmacologically acceptable acid addition salts thereof when $X_1$ is $-CH_2NL_2L_3$, (5) $-COR_{52}$, wherein $R_{52}$ is $(C_1-C_4)$alkyl; and wherein $Y_1$ is trans—CH=CH—, cis—CH=CH—, $-CH_2CH_2-$, or $-C\equiv C-$;

with the proviso that $X_1$ is -$COOR_1$ wherein $R_1$ is hydrogen or alkyl, $Z_1$ is trans—CH=CH— or —$CH_2CH_2-$, $R_7$ is alkyl, phenyl optionally substituted, or phenoxy optionally substituted, and wherein $L_1$ is $\alpha$-$R_3$:$\beta$-$R_4$, $\alpha$-$R_4$:$\beta$-$R_4$ or a mixture thereof and $M_1$ is $\alpha$-$R_5$:OH or $\alpha$-OH:$\beta R_5$ only when Z is other than —$(CH_2)_5$—or cis—CH=CH—$(CH_2)_3$ which comprises:

(1) optionally protecting alcoholic or carboxylic functional groups of a prostaglandin A compound corresponding to said 11-deoxy-11α-$(C_1-C_4)$-alkyl-prostaglandin E compound;

(2) reacting said prostaglandin A compound, or the functionally protected derivative thereof of step (1), with a $(C_1-C_4)$ alkyllithium complex, wherein the alkyl group of said alkyllithium complex is the same as the 11α-alkyl moiety of said 11-deoxy-11α-alkylprostaglandin E compound;

(3) optionally deprotecting the reaction product of step (2) in the event such protection was employed in step (1); and (4) recovering 11α-isomer from the reaction product of step (2) or step (3), with the proviso that steps (3) and (4) are interchangeable. More particularly the present invention provides a process wherein said 11α-alkylprostaglandin E compound is an 11-deoxy-11α-methylprostaglandin E compound and said alkyllithium complex is a methyllithium complex.

The present invention also particularly provides:

An 11-deoxy-11α-alkylprostaglandin E compound of formula II wherein $Z_1$, $X_1$, $Y_1$, $M_1$, $L_1$, and $R_7$ are as defined above; and wherein $R_6$ is $(C_1-C_4)$alkyl;

with the proviso that $X_1$ is -$COOR_1$ wherein $R_1$ is hydrogen or alkyl, $Z_1$ is trans—CH=CH— or —$CH_2CH_2-$, $R_7$ is alkyl, phenyl optionally substituted, or phenoxy optionally substituted, and wherein $L_1$ is $\alpha$-$R_3$:$\beta$-$R_4$, $\alpha$-$R_4$:$\beta$-$R_4$ or a mixture thereof and $M_1$ is $\alpha$-$R_5$:OH or $\alpha$-OH:$\beta R_5$ only when Z is other than —$(CH_2)_5$— or cis—CH=CH—$(CH_2)_3$.

Preferred compounds of formula II are those wherein $R_6$ is methyl.

Also particularly preferred are compounds selected from the group consisting of:

(a) 11-deoxy-11α,16,16-trimethyl-$PGE_2$, p-acetamidobenzamidophenyl ester;

(b) (16RS)-11,15-dideoxy-11α,16-dimethyl-16-hydroxy-$PGE_1$ or an ester of pharmacologically acceptable salt thereof; and (c) 2-Acetyl-2-decarboxy-11-deoxy-11α,16, 16-trimethyl-$PGE_2$.

Prostaglandin E compounds are those derivatives of prostanoic acid (formula III) wherein the C-9 position is substituted by an oxo group and the C-11 position is substituted by a hydroxyl group of the alpha configuration. Additionally, prostaglandin E compounds typically include an oxygenated substitutent at C-15 (oxo or hydroxy), the most prevalent such substituent being α-hydroxy group. While the naturally occuring prostaglandin E compounds additionally contain olefinic unsaturation at the C-5,6 and/or C-13,14 positions cis and/or trans, respectively, additional variations of the C-8 alpha side chain and C-12 beta side chain are also known among such compounds. Also especially known are derivatives of the C-1 carboxyl group, most especially salts and esters.

The present invention relates to 11-deoxy-11α-alkyl-prostaglandin E compounds prepared from corresponding prostaglandin A compounds. In such 11-deoxy-11α-alkylprostaglandins the β-hydroxyl substituent normally present at C-11 is replaced by an alkyl group also of the alpha configuration. The prefered alkyl group is methyl. The preparation of these 11-deoxy-11α-alkyl-prostaglandin E compound in accordance with the present invention is through a process wherein prostaglandin A compounds are utilized as starting materials. The prostaglandin A compounds are those which correspond to the 11-deoxy-11α-alkylprostaglandin E compounds to be prepared except that the prostaglandin A compounds exhibit an endocyclic olefinic double bond between C-10 and C-11 in place of the 11α-hydroxyl substituent. Such prostaglandin A compounds are typically prepared from the corresponding prostaglandin E compound by dehydration under acidic conditions. Such dehydration readily occurs in the β-hydroxy ketones represented by the prostaglandin E compounds.

In accordance with the present invention the prostaglandin A compounds are converted to 11-deoxy-11α-methylprostaglandin E compounds utilizing alkyllithium complex. In accordance with the discussion above, the preferred alkyllithium complex is a methyllithium complex. The methyllithium complex can be prepared by reacting copper (I) iodide and methyllithium in situ, thereby yielding a dialkyl copper lithium reagent. Thereafter, in accordance with procedures known in the art, the conjugate addition of the alkyl group to the α,β-unsaturated ketone (the prostaglandin A compound) is accomplished. See House, H. O., et al., J. Organic Chemistry 31:3128 (1966) and Corey, E. J., et al., JACS 89:3911 (1967).

Ordinarily, the resulting product is the desired 11α-alkyl epimer, although in cases were byproducts are produced, the 11α-alkylprostaglandin E compound can be separated from such resulting byproducts by ordinary chemical or physical means. For example, crystallization or chromatography represent such means.

Further in accordance with the process of the present invention, alcoholic or carboxycyclic functional groups of the prostaglandin A compound may be protected by known protective groups for use with prostaglandins prior to treatment with the alkyllithium complex. Accordingly, following the conversion of the protected derivative of the prostaglandin A compound to the corresponding 11-deoxy-11α-alkylprostaglandin E compound, deprotection is accomplished by known means and the resulting 11-deoxy-11α-alkylprostaglandin E end product prepared.

A variety of such protective groups can be employed by methods known in the art. For example, protection of carboxylic acids is accomplished by conversion to corresponding ester groups, especially lower alkyl esters, particularly methyl. For hydroxyl or alcoholic functional groups, any number of a variety of groups for which deprotection can be readily accomplished are employed. Such protective groups include, therefore, any group which replaces a hydroxy hydrogen and is neither attacked by nor is reactive to the reagents used in the transformations used herein as a hydroxy is and which is subsequently replaceable by acid hydrolysis with hydrogen in the preparation of the prostaglandin-type compounds. Several such protective groups are known in the art, e.g., tetrahydropyranyl and substituted tetrahydropyranyl. See for reference E. J. Corey, Proceedings of the Robert A. Welch Foundation Conferences on Chemical Research, XII Organic Synthesis, pgs. 51–79 (1969). Those blocking groups which have been found useful include:

(a) tetrahydropyranyl;
(b) tetrahydrofuranyl;
(c) a group of the formula —C(OR$_{11}$)(R$_{12}$)—CH(R$_{13}$)(R$_{14}$), wherein R$_{11}$ is alkyl of one to 18 carbon atoms, inclusive, cycloalkyl of 3 to 10 carbon atoms, inclusive, aralkyl of 7 to 12 carbon atoms, inclusive, phenyl or phenyl substituted with one to 3 alkyl of one to 4 carbon atoms, inclusive, wherein R$_{12}$ and R$_{13}$ are alkyl of one to 4 carbon atoms, inclusive, phenyl, phenyl substituted with one, 2 or 3 alkyl of one to 4 carbon atoms, inclusive, or when R$_{12}$ and R$_{13}$ are taken together —(CH$_2$)$_a$— or when R$_{12}$ and R$_{13}$ are taken together —(CH$_2$)$_b$—O—(CH$_2$)$_c$, wherein a is 3, 4, or 5 and b is one, 2, or 3, and c is one, 2, or 3, with the proviso that b plus c is 2, 3, or 4, with the further proviso that R$_{12}$ and R$_{13}$ may be the same or different, and wherein R$_{14}$ is hydrogen or phenyl; and
(d) silyl groups according to R$_{28}$, as qualified hereinafter.

When the protective group is tetrahydropyranyl, the tetrahydropyranyl ether derivative of any hydroxy moieties of the PG-type intermediates herein is obtained by reaction of the hydroxy-containingcompound with 2,3-dihydropyran in an inert solvent, e.g., dichloromethane, in the presence of an acid condensing agent such as p-toluenesulfonic acid or pyridine hydrochloride. The dihydropyran is used in large stoichiometric excess, preferably 4 to 100 times the stoichiometric amount. The reaction is normally complete in less than an hour at 20°–50° C.

When the protective group is tetrahydrofuranyl, 2,3-dihydrofuran is used, as described in the preceding paragraph, in place of the 2,3-dihydropyran.

When the protective group is of the formula —C(OR$_{11}$)(R$_{12}$)—Ch(R$_{13}$)(R$_{14}$), wherein R$_{11}$, R$_{12}$, R$_{13}$, and R$_{14}$ are as defined above; a vinyl ether or an unsaturated cyclic or heterocyclic compound, e.g., 1-cyclohexen-1-yl methyl ether, or 5,6-dihydro-4-methoxy-2H-pyran is employed. See C. B. Reese, et al., J. American Chemical Society 89, 3366 (1967). The reaction conditions for such vinyl ethers and unsaturated compounds are similar to those for dihydropyran above.

R$_{28}$ is a silyl protective group of the formula —Si(G$_1$)$_3$. In some cases, such silylations are general, in that they silylate all hydroxyls of a molecule, while in other cases they are selective, in that while one or more hydroxyls are silylated at least one other hydroxyl remains unaffected. For any of these silylations, silyl groups within the scope of —Si(G$_1$)$_3$ include trimethylsilyl, dimethylphenylsilyl, triphenylsilyl, t-butyldimethylsilyl, or methylphenylbenzylsilyl. With regard to G$_1$, examples of alkyl are methyl, ethyl, propyl, isobutyl, butyl, sec-butyl, tert-butyl, pentyl, and the like. Examples of aralkyl are benzyl, phenethyl, α-phenylethyl, 3-phenyl propyl, α-naphthylmethyl, and 2-(α-naphthyl)ethyl. Examples of phenyl substituted with halo or alkyl are p-chlorophenyl, m-fluorophenyl, o-tolyl, 2,4-dichlorophenyl, p-tert-butylphenyl, 4-chloro-2-methylphenyl, and 2,4-dichloro-3-methylphenyl.

These silyl groups are known in the art. See for example, Pierce, "Silylation of Organic Compounds," Pierce Chemical Company, Rockford, Ill. (1968). When silylated products of the charts below are intended to be subjected to chromatographic purification, then the use of silyl groups known to be unstable to chromatography (e.g., trimethylsilyl) is to be avoided. Further, when silyl groups are to be introduced selectively, silylating agents which are readily available and known to be useful in selective silylations are employed. For example, t-butyldimethylsilyl groups are employed when selective introduction is required. Further, when silyl groups are to be selectively hydrolyzed in the presence of protective groups according to R$_{10}$ or acyl protective groups, then the use of silyl groups which are readily available and known to be easily hydrolyzable with tetra-n-butylammonium fluoride are employed. A particularly useful silyl group for this purpose is t-butyldimethylsilyl, while other silyl groups (e.g., trimethylsilyl) are not employed when selective introduction and/or hydrolysis is required.

The protective groups are otherwise removed by mild acidic hydrolysis. For example, by reaction with (1) hydrochloric acid in methanol; (2) a mixture of acetic acid, water, and tetrahydrofuran, or (3) aqueous citric acid or aqueous phosphoric acid in tetrahydrofuran, at temperatures below 55° C., hydrolysis of the blocking group is achieved.

In addition to the acid hydrolizable protective groups referred to above, acyl protective groups may also be employed. For example, if a variable such as R$_9$ defined such acyl protective groups, such groups can include:

(a) benzoyl;
(b) benzoyl substituted with one to 5 alkyl or one to 4 carbon atoms, inclusive, or phenylalkyl of 7 to 12 carbon atoms, inclusive, or nitro, with the proviso that not more than two substituents are other than alkyl, and that the total number of carbon atoms in the substituents does not exceed 10 carbon atoms, with the further proviso that the substituents are the same or different;

(c) benzoyl substituted with alkoxycarbonyl of 2 to 5 carbon atoms, inclusive;

(d) naphthoyl;

(e) naphthoyl substituted with one to 9, inclusive, alkyl of one to 4 carbon atoms, inclusive, phenylalkyl of 7 to 10 carbon atoms, inclusive, or nitro, with the proviso that not more than two substituents on either of the fused aromatic rings are other than alkyl and that the total number of carbon atoms in the substituents on either of the fused aromatic rings does not exceed 10 carbon atoms, with the further proviso that the various substituents are the same or different; or (f) alkanoyl of 2 to 12 carbon atoms, inclusive.

In preparing these acyl derivatives of a hydroxy-containing compound herein, methods generally known in the art are employed. Thus, for example, an aromatic acid of the formula $R_9$ is as defined above (e.g., benzoic acid), is reacted with the hydroxy-containing compound in the presence of a dehydrating agent, e.g., p-toluenesulfonyl chloride or dicyclohexylcarbodiimide; or alternatively an anhydride of the aromatic acid of the formula $(R_9)OH$, e.g., benzoic anhydride, is used.

Preferably, however, the process described in the above paragraph proceeds by use of the appropriate acyl halide, e.g., $R_9Hal$, wherein hal is chloro, bromo, or iodo. For example, benzoyl chloride is reacted with the hydroxyl-containing compound in the presence of a hydrogen chloride scavenger, e.g., a tertiary amine such as pyridine, triethylamine or the like. The reaction is carried out under a variety of conditions, using procedures generally known in the art. Generally mild conditions are employed: 0°-60° C., contacting the reactants in a liquid medium (e.g., excess pyridine or an inert solvent such as benzene, toluene, or chloroform). The acylating agent is used either in stoichiometric amount or in substantial stoichiometric excess.

As examples of $R_9$, the following compounds are available as acids $(R_9OH)$, $(R_9)_2O$, or acyl chlorides $(R_9Cl)$: benzyl; substituted benzoyl, e.g., (2-, 3-, or 4-)methylbenzoyl, (2-, 3-, or 4-)ethylbenzoyl, (2-, 3-, or 4-)isopropylbenzoyl, (2-, 3-, or 4-)tert-butylbenzoyl, 2,4-dimethylbenzoyl, 3,5-dimethylbenzoyl, 2-isopropyltoluyl, 2,4,6-trimethylbenzoyl, pentamethylbenzoyl, phenyl(2-, 3-, or 4-)toluyl, (2-, 3-, or 4-)phenethylbenzoyl, (2-, 3-, or 4-)nitrobenzoyl, (2,4,2,5-, or 2,3-)dinitrobenzoyl, 2,3-dimethyl-2-nitrobenzoyl, 4,5-dimethyl-2-nitrobenzoyl, 2-nitro-6-phenylethylbenzoyl, 3-nitro-2-phenethylbenzoyl, 2-nitro-6-phenylethylbenzoyl, 3-nitro-2-phenethylbenzoyl; mono esterified phthaloyl, isophthaloyl, or terephthaloyl; 1- or 2-naphthoyl; substituted naphthoyl, e.g., (2-, 3-, 4-, 5-, 6-, or 7-)methyl-1-naphthoyl, (2- or 4-)ethyl-1-naphthoyl, 2-isopropyl-1-naphthoyl, 4,5-dimethyl-1-naphthoyl, 6-isopropyl-4-methyl-1-naphthoyl, 8-benzoyl-1-naphthoyl, (3-, 4-, 5-, or 8-)-nitro-1-naphthoyl, 4,5-dinitro-1-naphthoyl, (3-, 4-, 6-, 7-, or 8-)-methyl-1-naphthoyl, 4-ethyl-2-naphthoyl, and (5- or 8-)nitro-2-naphthoyl and acetyl.

There may be employed, therefore, benzoyl chloride, 4-nitrobenzoyl chloride, 3,5-dinitrobenzoyl chloride, or the like, i.e. $R_9Cl$ compounds corresponding to the above $R_9$ groups. If the acyl chloride is not available, it is prepared from the corresponding acid and phosphorus pentachloride as is known in the art. It is preferred that the $R_9OH$, $(R_9)_2O$, or $R_9Cl$ reactant does not have bulky hindering substituents, e.g., tert-butyl on both of the ring carbon atoms adjacent to the carbonyl attaching site.

The acyl protective groups, according to $R_9$, are removed by deacylation. Alkali metal carbonate or hydroxide are employed effectively at ambient temperature for this purpose. For example, potassium carbonate or hydroxide in aqueous methanol at about 25° C. is advantageously employed.

Because of the facility of the protection and deprotection steps, the preferred protective groups include trimethylsilyl, although other protective groups such as t-butyldimethylsilyl are also highly useful.

The novel compounds of formula II are all useful in existing biological effects of the corresponding PGE compounds. In particular, they are useful agents for the prevention and treatment of ulcers in the gastrointestinal tract. Accordingly, they are used for these antiulcer purposes by methods knonw in the art for the use of corresponding PGE compounds. See U.S. Pat. Nos. 4,081,553, 4,097,603, 3,927,213, 4,123,463, 4,088,784, 3,903,297, 3,911,124, 3,917,828, 4,061,742, 3,928,588, and 3,781,429, incorporated here by reference for the manner of use of the novel formula II compounds herein as antiulcer agents.

Thus, the novel prostaglandin analogs of the present invention are all useful pharmacological agents, exhibiting high potency as gastrointestinal cytoprotective agents. The gastrointestinal cytoprotective property of the novel prostaglandin analogs herein is evidenced by the ability of these compounds to inhibit the formation of ulcers or other lesions in standard laboratory animals treated with gastrointestinally erosive agents. For a discussion of such laboratory tests, describing the prevention of these gastric lesions by pretreatment with prostaglandins, see Robert, et al., "Gastric Cytoprotective Property of Prostaglandins", Gastroenterology 72:1121 (1977); and a discussion of such laboratory tests, describing the reduction in intestinal lesions by pretreatment with prostaglandins, see Robert, et al., Gastroenterology 69:1045 (1974), wherein, inter alia, $PGE_2$ is demonstrated to be effective in reducing indomethacin-induced intestinal lesions in the rat.

By virtue of the gastrointestinal cytoprotective property of the novel prostaglandin analogs herein, these compounds are highly useful in the prevention and treatment of inflammatory diseases of the stomach, duodenum, and large and small intestine. For example, the novel prostaglandin analogs herein are employed as gastric cytoprotective agents in the prevention and treatment of gastric erosive diseases, such as gastric ulceration and erosive gastritis. Moreover, the novel prostaglandin analogs herein are useful as intestinal cytoprotective agents in the treatment of numerous intestinal inflammatory diseases, included in which are Crohn's disease, inflammatory bowel disease, infectious enteritis, sprue, and intestinal inflammatory diseases secondary to radiation exposure or allergen exposure. While the novel prostaglandin analogs herein are useful for the present gastrointestinal cytoprotective purposes in a wide variety of mammals, including valuable domestic animals, the principal use of the novel prostaglandin analogs herein is in man.

Accordingly, by this preferred embodiment of the gastric cytoprotective use, the novel prostaglandin analogs herein are used in man for the treatment and prevention of gastric ulcer, duodenal ulcer, gastritis and other gastric inflammatory conditions (e.g., secondary to radiation exposure), by the systemic administration of a dose of a novel prostaglandin analog effective to treat or prevent the development of the disease. In the prophylactic use of these gastric cytoprotective prostaglandins, patients are selected for treatment who exhibit a high susceptibility to the acquisition of a gastric inflammatory disease. Examples of such patients include those with a previous history of gastric or duodenal ulcer; those persons subjected to chronic or acute and stressful environmental conditions, whether of a physical or emotional origin; those manifesting chronic and excessive ethanol consumption (e.g., especially persons diagnosed as alcoholics); and those persons for whom an acute exposure to a cytodestructive does of ionizing radiation is contemplated. In the latter case, the use of the novel prostaglandin analogs herein in patients receiving therapeutic doses of radiation, for example in the treatment of neoplastic diseases, is particularly contemplated.

When the novel prostaglandin analogs herein are employed as enteric cytoprotective agents, the prophylactic or therapeutic use is undertaken when the animal or patient is in a state of high susceptibility to the development of an intestinal inflammatory disease or the diagnosis of such a disease has been made. Examples of patients exhibiting a high susceptibility to the development of enteric inflammatory diseases include, for example, patients subject to cytodestructive doses of radiation, as indicated above.

With regard to the systemic administration of the novel compounds of the present invention, any convenient systemic route is employed, although oral administration is the highly preferred route. While the oral route is preferred, for patients where ths route of administration is inconvenient or unacceptable, other routes such as via a nasogastric tube or via suppositories and enemas are likewise preferred. For a description of the various methods of formulation and routes of administration by which the novel prostaglandin analogs herein are employed, see U.S. Pat. No. 3,903,297.

The dosage regimen and duration of treatment for the novel prostaglandin analogs herein will depend upon a wide variety of factors, including the type, age, weight, sex, medication condition of the animal or patient being treated and the nature and severity of the gastric or enteric inflammatory disease to be treated or prevented. For example, oral doses between 25 mg/kg/day and 0.5 µg/kg/day will ordinarily be gastrointestinally cytoprotective. Once a minimum effective dose for the particular novel prostaglandin analog herein is determined for a particular animal or patient, that animal or patient is thereafter advantageously provided with a daily dosage schedule which will provide a substantially uniform level of the novel cytoprotective analog throughout the day.

Moreover, treatment with the novel prostaglandin analogs herein should be continued therapeutically until the gastrointestinal inflammatory disease has been successfully arrested, and thereafter a prophylactic regimen with the prostaglandin analog should be maintained until susceptibility to the recurrence of the disease is no longer high. Thus, in the case of an acute exposure to a noxious agent, treatment for several days to several weeks will ordinarily be sufficient. However, in cases where a patient, for example, has a history of multiple recurrences of gastric or duodenal ulcer, prophylactic treatment may be maintained indefinitely, based upon the continued tolerance to the drug.

DESCRIPTION OF THE PREFERRED EMBODIMENTS

The present invention is more completely understood by the operation of the following examples:

EXAMPLE 1

11-Deoxy-11α-methyl-PGE$_2$ (Formula I: $X_1$ is —COOH, $Z_1$ is cis—CH=CH—(CH$_2$)$_3$—, $Y_1$ is trans—CH=CH—, $M_1$ is α-OH:β-H, $R_3$ and $R_4$ of $L_1$ are both hydrogen, and $R_7$ is n-butyl).

A. Bis-(trimethylsilyl)-derivative of PGA$_2$

Solution of 999 mg of PGA$_2$ in 25 ml of tetrahydrofuran is treated with 10 ml of hexamethyldisilazane and 3 ml of trimethylchlorosilane, and the resulting mixture was stirred for 18 hr at room temperature under a nitrogen atmosphere. The solvents are then removed at reduced pressure (35° maximum temperature) to remove excess hexamethyldisilazane. The residue is dissolved in 50 ml of xylene, filtered and concentrated at reduced pressure. The xylene azeotrope procedure is repeated once more (without filtering), thereby affording 1.52 g of the desired bis(trimethylsilyl) derivative.

B. 11-Deoxy-11α-methyl-PGE$_2$

All glassware is first flame-dried under a nitrogen atmosphere. A suspension of 1.14 g of cuprous iodide in 40 ml of anhydrous ether is cooled to −5° C. and treated with 7.3 ml of 1.64M ethereal methyllithium. To the resulting clear solution is added a solution of 1.52 g of the product of part A in 15 ml of anhydrous ether. The addition is done dropwise, with rapid magnetic stirring over about 2–3 minutes at −5° C. After 15 min longer at −5°, the mixture is poured slowly into a vigorously stirred solution of aqueous ammonium chloride. The product is extracted with diethyl ether, washed with brine, dried over anhydrous sodium sulfate and concentrated at reduced pressure. The resulting product is taken up in 50 ml of ether and filtered through diatomaceous earth to remove the finely-divided copper-containing precipitate. After removal of the diethyl ether, the crude product is taken up in 20 ml of ethanol and water is added until the mixture becomes cloudy (~10–15 ml). Three drops of glacial acetic acid are added and the mixture is stirred under nitrogen for three hours at room temperature. By this time, TLC (thin layer chromatography) yields one spot, slightly less polar than PGA$_2$. After removal of the ethanol at 35° on the rotary evaporator, the residue is diluted with water and extracted with diethyl ether. The combined ether layers are washed with brine, dried over sodium sulfate and concentrated at reduced pressure. The light yellow viscous oil thusly obtained (1.8 g) is chromatographed on 100 g of acid-washed silica gel wet-packed in 305 ethyl acetate-hexane. For elution of the column, a gradient was used consisting of 2 l. of 30% ethyl acetate-hexane and 2 l. of pure ethyl acetate (50 ml fractions). Fractions 13–41 are homogeneous by TLC and are combined. This product (500 mg) which crystallized on standing, was recrystallized from ether-hexane, yielding 380 mg of title product, m.p. 73°–74°.

IR absorptions are observed at: 3340, 3000, 2720, 2660, 2580, 1725, 1675, 1325, 1295, 1250, 1175, 1020, 1000, 980, 895, 740 cm$^{-1}$.

NMR absorptions are observed at: 6.8, 5.70–5.25, 4.15, and 1.15 δ.

Mass spectrum peaks are observed at: 350, 332, 314, 279, 261, and 243.

EXAMPLE 2

11-Deoxy-11α, 16,16-trimethyl-PGE$_2$

A. 16,16-dimethyl-PGA$_2$, methyl ester-15-(t-butyl-dimethyl silyl ether).

A 250 ml one neck flask, equipped with magnetic stirring bar and a nitrogen inlet tube is charged with 5.85 g 16,16-dimethyl-PGA$_2$, methyl ester and 25 ml of dry dimethylformamide. The solution is cooled to 0° C. and 3.15 g of imidazole followed by 3.48 g of t-butyldimethylsilyl chloride are added. The reaction is stirred at 0° for 4 hr and at room temperature for 16 hr and is diluted with brine and extracted with ethyl acetate. The combined extracts are washed successively with a solution of 1:1 brine and 1M aqueous potassium bisulfate, saturated sodium bicarbonate, and bine. The organic layer is dried over Na$_2$SO$_4$ and concentrated in vacuo. Chromatography on a column slurry-packed with 400 g of silica gel 60 and 15% ethyl acetate in Skellysolve B yields a residue of 5.72 g of partially purified product. The 48 mm × 30 in column is then slurry packed with 400 g of silica gel 60 (E. Merck) in methylene chloride and partially purified product is applied in methylene chloride and eluted successively with 2 l of methylene chloride, 2 l of 1% acetone in methylene chloride and 3 l of 2% acetone in methylene. Fractions contained 45 ml each after the first two 1000 ml fractions. Based on TLC homogeneity, fractions 50–82 were combined to afford 4.01 g (53%) of pure product.

NMR absorptions (CDCl$_3$; TMS) are observed at: 0.02, 0.05, 0.83, 0.87, 0.95, 0.79–2.68, 3.132–3.41, 3.69, 3.65–3.84, 5.28–5.64, 6.21 and 7.50 δ.

Infrared absorptions are observed at: 2950, 2930, 2840, 1738, 1708, 1580, 1475, 1458, 1438, 1382, 1350, 1250, 1162, 1050, 1000, 980, 860, 830, and 760 cm$^{-1}$.

Silica gel TLC R$_f$ is 0.29 in 2% acetone in methylene chloride.

B. 11-deoxy-11α,16,16-trimethyl-PGE$_2$, methyl ester, 15-(t-butyldimethylsilyl ether).

An oven dried, three neck, 100 ml flask equipped with magnetic stirring bar, addition funnel, and nitrogen-vacuum connection is charged with 0.78 g (4.08 mmol) of cuprous iodide and 30 ml of dry diethyl ether, then is alternately degassed and flushed with nitrogen and cooled to 0° C. To the cold solution is added 5.8 ml of 1.4 M ethereal methyllithium dropwise. When the addition is complete the solution turned from yellow to colorless, and 1.0 g of the product of part A in 10 ml of diethyl ether is added dropwise over a 6 min period. Residual product is rinsed into the flask with ether and the yellow mixture stirred for 15 min at 0° when glacial acetic acid, 2 ml, is added cautiously. The thick suspension is diluted with brine and extracted, with ether. The combined extracts are washed with saturated aqueous sodium bicarbonate and brine, dried over sodium sulfate and concentrated in vacuo to afford 1.02 g (99%) of product, an orange colored oil.

NMR absorption (CDCl$_3$, TMS) are observed at: 0.05, 0.11, 0.83, 0.85, 0.91, 0.80–2.72, 3.64, 3.77, and 5.22–5.58.

Infrared absorptions are observed at: 2960, 2940, 2050, 1740, 1479, 1460, 1430, 1415, 1380, 1366, 1250, 1160, 1055, 1000, 980, 940, 910, 860, 830, 770, and 670 cm$^{-1}$.

Silica Gel TLC R$_f$ is 0.58 in ethylacetate and Skellysolve B (1:3).

C. 11-deoxy-11α, 16,16-trimethyl-PGE$_2$, methyl ester.

A 100 ml, one neck flask, equipped with a magnetic stirring bar and nitrogen-vacuum connection is charged with 4.14 g of the product of part B and 20 ml of tetrahydrofuran, and then alternately degassed and flushed with nitrogen. To the solution is added 30 ml of 0.75 M tetrabutylammonium fluoride and the reaction is refluxed overnight, cooled to room temperature, diluted with diethyl ether, and shaken with brine containing 0.5 M potassium bisulfate. The ethereal layers are washed with brine, dried over Na$_2$SO$_4$ and concentrated in vacuo to afford a brown residue which TLC revealed to contain product. The brown residue is suspended in a solution of 20:10:3 acetic acid-water-tetrahydrofuran and was stirred at 45° C. for 8 hr and at room temperature overnight. After the reaction has been diluted with brine and acidified to pH 2-14 3 with 0.5 M potassium bisulfate, it is extracted with diethyl ether. The combined extracts are washed with water and brine, dried over Na$_2$SO$_4$ and concentrated in vacuo to afford 3.1 g of product (ester) plus the corresponding carboxylic acid from hydrolysis.

A 500 ml, one neck flask equipped with magnetic stirring bar and nitrogen-vacuum connection is charged with 3.1 g of the product above and 200 ml of acetonitrile. The solution is alternately degassed and flushed with nitrogen after which 14.2 ml of diisopropylethylamine and 4.1 ml (65.4 mmol) of methyl iodide are added. The reaction was stirred under a nitrogen atmosphere for 72 hr and was then diluted with brine and extracted with ethyl acetate. The combined extracts are washed with 0.5 M aqueous potassium bisulfate, aqueous saturated bicarbonate, and brine, dried over Na$_2$SO$_4$ and concentrated in vacuo to give a dark brown oil. A 48 mm × 30 min column is slurry-packed in 400 g of Silica Gel 60 (E. Merck) in 1:3 ethyl acetate-Skellysolve B. The dark oil is loaded in Skellysolve B and eluted with ethyl acetate and Skellysolve B (1:3). Fractions contained 30 ml after the initial 600 ml fraction. Based on TLC homogeniety fractions 20–24 are combined to yield 2.40 g of pure product.

NMR absorptions (CDCl$_3$, TMS) are observed at: 0.82, 0.86, 0.78–2.67, 3.61, 3.72–3.92, and 5.22–5.69 δ.

Infrared absorptions are observed at: 3500, 2950, 2870, 1735, 1460, 1440, 1410, 1375, 1360, 1320, 1240, 1160, 1050, 1020, 970, and 735 cm$^{-1}$.

Silica Gel TLC R$_F$ is 0.23 in 1:3 ethyl acetate-Skellysolve B.

D. 11-deoxy-11α,16,16-trimethyl-PGE$_2$

A 100 ml one neck flask equipped with magnetic stirring bar and nitrogen inlet tube is charged with 0.55 g of product of part C. The residue is diluted with 10 ml of methanol and 5 ml of 10% aqueous potassium hydroxide and then stirred at room temperature for 6 hour. The basic mixture is acidified to pH 2-3 with 1N hydrochloric acid, diluted with brine, and extracted with ethyl acetate. The combined extracts are washed with brine, dried over Na$_2$SO$_4$ and concentrated in vacuo to afford 0.53 g of title product as a pale yellow oil. The yellow residue is filtered through 40 g of Silica Gel 60 (deactivated with 10% water by weight), slurry-packed and eluted with 35% ethyl acetate in Skellysolve B. After concentration in vacuo of fractions which by TLC contained pure product, 0.53 g (100%) of product is obtained.

NMR absorptions (CDCl$_3$, TMS) are observed at: 0.86, 0.89, 0.57–2.73, 3.88, 5.25–5.75, and 6.78 δ.

Infrared absorptions are observed at: broad 3440, 2950, 1730, broad 1710, 1450, 1400, 1370, 1240, 1160, 1050, 970, 730 cm$^{-1}$.

Silica Gel TLC Rf is 0.29 in 35% ethyl acetate, 64% Skellysolve B, 1% acetic acid.

Following the procedures of the examples described above but using ethyllithium, propyllithium, or butyllithium in place of methyl-lithium the corresponding 11-deoxy-11α-alkyl-16,16-dimethylprostaglandin E compounds are prepared. Further, employing other known PGA compounds, each of the various corresponding 11-deoxy-11α-alkylprostaglandin E compounds is prepared.

FORMULAS

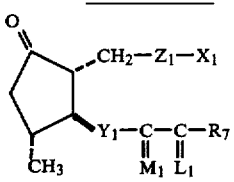

I

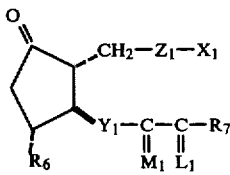

II

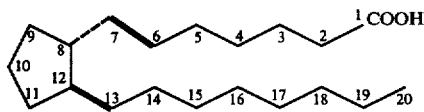

III

I claim:

1. An 11-deoxy-11α-alkylprostaglandin E compound of formula II

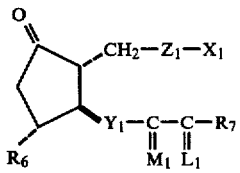

II wherein Z$_1$ is (1) cis—CH=CH—CH$_2$—(CH$_2$)$_g$—C(R$_2$)$_2$—,
(2) cis—CH$_2$CH=CH—(CH$_2$)$_g$—CH$_2$—,
(3) trans—(CH$_2$)$_2$—(CH$_2$)$_g$—CH=CH—,
(4) —(CH$_2$)$_3$—(CH$_2$)$_g$—C(R$_2$)$_2$—,
(5) —CH$_2$—O—CH$_2$—(CH$_2$)$_g$—CH$_2$—,
(6) —(CH$_2$)$_2$—O—(CH$_2$)$_g$—CH$_2$—,
(7) —(CH$_2$)$_3$—O—(CH$_2$)$_g$—, or
(8) —(m—Ph)—Z$_3$—(CH$_2$)$_g$—, wherein R$_2$ is hydrogen or fluoro, g is one, two, or three, Z$_3$ is oxa or methylene, and (m—Ph) is inter-meta-phenylene;

wherein X$_1$ is —COR$_{52}$, wherein R$_{52}$ is (C$_1$–C$_4$)alkyl;

wherein Y$_1$ is trans—CH=CH—, cis—CH=CH—, —CH$_2$CH$_2$—, or —C≡C—;

wherein L$_1$ is α—R$_3$:β—R$_4$, α—R$_4$:β—R$_3$, or a mixture of α—R$_3$:β—R$_4$ and α—R$_4$:β—R$_3$ wherein R$_3$ and R$_4$ are hydrogen, methyl, or fluoro, being the same or different, with the proviso that one of R$_3$ and R$_4$ is fluoro only when the other is hydrogen or fluoro and M$_1$ is α—OH:β—R$_5$ or α—R$_5$:b—OH, wherein R$_5$ is hydrogen or methyl or wherein L$_1$ is α—OH:β—R$_5$ or α—R$_5$:β—OH and M$_1$ is α—H:-β—H;

wherein R$_7$ is (1) —C$_m$H$_{2m}$—CH$_3$, wherein m is an integer from one to 5, inclusive,
(2) phenoxy optionally substituted by one, two or three chloro, fluoro, trifluoromethyl, (C$_1$–C$_3$)alkyl, or (C$_1$–C$_3$)alkoxy, with the proviso that not more than two substituents are other than alkyl, with the proviso that R$_7$ is phenoxy or substituted phenoxy, only when R$_3$ and R$_4$ are hydrogen or methyl, being the same or different,
(3) phenyl, benzyl, phenylethyl, or phenylpropyl optionally substituted on the aromatic ring by one, two, or three chloro, fluoro, trifluoromethyl, (C$_1$–C$_3$)alkyl, or (C$_1$–C$_3$)alkoxy, with the proviso that not more than two substituents are other than alkyl,
(4) cis—CH=CH—CH$_2$—CH$_3$,
(5) —(CH$_2$)$_2$—CH(OH)—CH$_3$, or
(6) —(CH$_2$)$_3$—CH=C(CH$_3$)$_2$;

wherein —C(L$_1$)—R$_7$ taken together is (1) (C$_4$–C$_7$)cycloalkyl optionally substituted by one to 3 (C$_1$–C$_5$)alkyl;
(2) 2-(2-furyl)ethyl,
(3) 2-(3-thienyl)ethoxy, or
(4) 3-thienyloxymethyl; and wherein R$_6$ is (C$_1$–C$_4$)alkyl.

2. A compound according to claim 1, 2-acetyl-2-decarboxy-11-deoxy-11α,16,16-trimethyl-PGE$_2$.

* * * * *

UNITED STATES PATENT OFFICE

CERTIFICATE OF CORRECTION

Patent No. 4,477,684  Dated 16 October 1984

Inventor(s) Gordon L. Bundy

It is certified that error appears in the above-identified patent and that said Letters Patent are hereby corrected as shown below:

Column 1, line 29
"11deoxy-11α"

should read
-- 11-deoxy-11α --

Column 3, line 25
"is other hydrogen,"

should read
-- is other than hydrogen, --

Column 4, line 6
"or α-OH:βR$_5$"

should read
-- or α-OH:β-R$_5$

Column 4, line 38
"the β-hydroxyl"

should read
-- the α-hydroxyl --

Column 8, line 20
"methods knonw"

Page 11, line 20
-- methods known --

Column 9, line 15
"cytodestructive does"

should read
-- cytodestructive dose --

Column 10, line 56
"wet-packed in 305"

should read
-- wet-packed in 30% --

UNITED STATES PATENT OFFICE

CERTIFICATE OF CORRECTION

Patent No. 4,477,684　　　　　Dated 16 October 1984

Inventor(s) Gordon L. Bundy

It is certified that error appears in the above-identified patent and that said Letters Patent are hereby corrected as shown below:

Column 12, line 21　　　　　should read
　"pH 2-14 3 with"　　　　　　-- pH 2-3 with --

Signed and Sealed this

Thirteenth Day of August 1985

[SEAL]

Attest:

DONALD J. QUIGG

Attesting Officer　　Acting Commissioner of Patents and Trademarks